(12) United States Patent
Yankelevitz et al.

(10) Patent No.: US 7,693,729 B2
(45) Date of Patent: Apr. 6, 2010

(54) SYSTEM AND METHOD FOR CONDUCTING A CLINICAL TRIAL STUDY

(75) Inventors: David Yankelevitz, Brooklyn, NY (US); Claudia Henschke, New York, NY (US); Anthony P. Reeves, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 1455 days.

(21) Appl. No.: 10/901,362

(22) Filed: Jul. 28, 2004

(65) Prior Publication Data

US 2006/0026034 A1    Feb. 2, 2006

(51) Int. Cl.
    G06Q 10/00    (2006.01)
(52) U.S. Cl. ............... 705/2; 705/3; 705/1; 707/104.1
(58) Field of Classification Search ............ 705/2, 705/1, 3
    See application file for complete search history.

(56) References Cited

U.S. PATENT DOCUMENTS

| | | | |
|---|---|---|---|
| 4,945,476 A | 7/1990 | Bodick | |
| 5,950,207 A | 9/1999 | Mortimore | |
| 5,991,731 A * | 11/1999 | Colon et al. | 705/3 |
| 6,260,021 B1 | 7/2001 | Wong | |
| 6,574,518 B1 | 6/2003 | Lounsberry | |
| 6,603,494 B1 | 8/2003 | Banks | |
| 6,611,846 B1 | 8/2003 | Stoodley | |
| 6,621,918 B1 | 9/2003 | Hu | |
| 6,687,329 B1 | 2/2004 | Hsieh | |
| 7,251,609 B1 * | 7/2007 | McAlindon et al. | 705/3 |
| 2002/0019751 A1 | 2/2002 | Rothschild | |
| 2003/0097291 A1 | 5/2003 | Freedman | |
| 2004/0010418 A1 | 1/2004 | Buonocore et al. | |
| 2005/0256745 A1 * | 11/2005 | Dalton | 705/3 |

* cited by examiner

Primary Examiner—Gerald J. O'Connor
Assistant Examiner—Hiep Nguyen
(74) Attorney, Agent, or Firm—Citadel Patent Law; George A. Leone, Sr.

(57) ABSTRACT

Described is a method and system for conducting a clinical trial. Medical data is obtained from a patient participating in the clinical trial. Then, the medical data and at least one identifier are transmitted, via a communications network, for storage at a remote server. The at least one identifier links the medical data to a record of the patient. Access to at least portions of the medical data is provided, via the communications network, to trial participants based on predefined clinical trial procedures. The remote server tracks accessing of the medical data by the trial participants and generation by the trial participants of work product responsive to the medical data.

12 Claims, 4 Drawing Sheets

MFMDR 200

CTMDR 212

Updated STMDR 218

CTP 300

SYSTEM AND METHOD FOR CONDUCTING A CLINICAL TRIAL STUDY

BACKGROUND

Clinical trials of pharmaceutical/medical products are lengthy and expensive due in part to delays resulting from inefficiencies in communications between participants in the trial. For certain products, each day by which the introduction to the market is delayed may cost the pharmaceutical company millions of dollars.

In a typical case, review and transfer of medical data, such as radiology data ("R/D") including radiology image data, and related reports as currently handled among clinical trial participants unduly delay the clinical trial process. Typically, participants may transmit the medical data, including image data and related reports, by courier, mail or other document delivery services. Each such communication may delay the progress of the clinical trials by one or more days.

For example, in the case of radiology images, a radiologist reviews the radiology data and generates a radiologist report. The report is forwarded to a physician for the patient who reviews the radiologist report and makes his own report. The patient physician then forwards both reports along with the radiology data to a monitoring facility for the clinical trial and/or directly to a clinical trial administrator group. The reports along with the corresponding radiology data are reviewed and processed at the respective facilities in accordance with clinical trial protocols and standards.

SUMMARY OF THE INVENTION

The present invention relates to a method and system for conducting a clinical trial. Medical data is obtained from a patient participating in the clinical trial. Then, the medical data and at least one identifier are transmitted, via a communications network, for storage at a remote server. The at least one identifier links the medical data to a record of the patient. Access to at least portions of the medical data is provided, via the communications network, to trial participants based on predefined clinical trial procedures. The remote server tracks accessing of the medical data by the trial participants and generation by the trial participants of work product responsive to the medical data.

DETAILED DESCRIPTION

The present invention may be further understood with reference to the following description of preferred exemplary embodiments and the related appended drawings. It should be understood that, although the preferred embodiment of the present invention will be described with reference to conducting clinical trials using radiology image data, the present invention may be implemented on a wide range of medical data including, for example, photographic image data, optical projection image data, image data of DNA chips, blood test report, etc., and the term "medical data" will be used throughout this description to generically refer to all such types of data.

Figure 1:
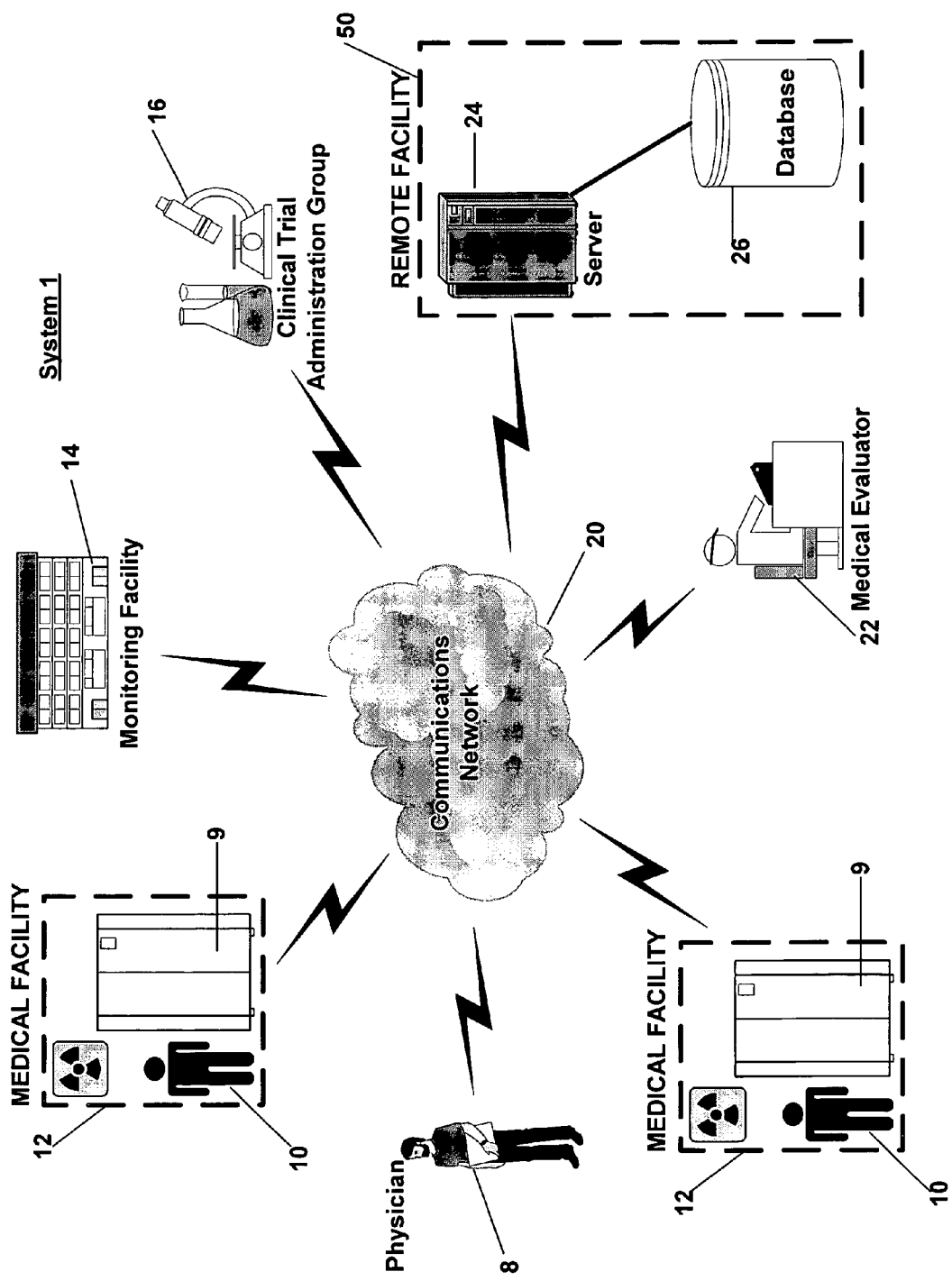
FIG. 1 shows an exemplary embodiment of a system of conducting a clinical trial study according to the present invention.
Figure 3:
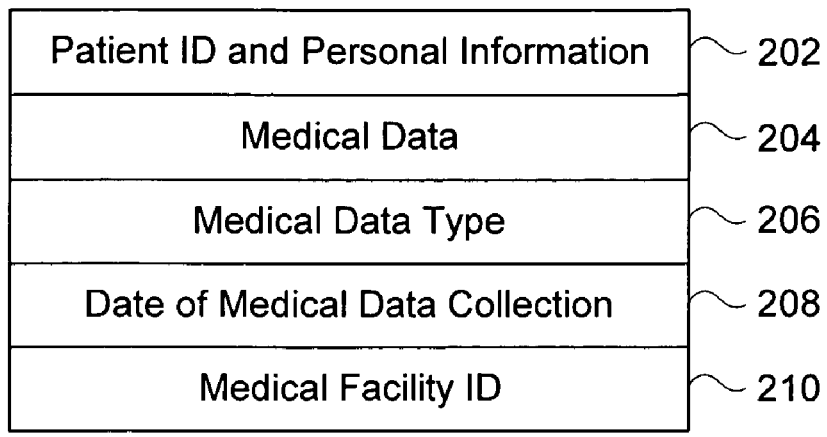
FIG. 3 shows an exemplary embodiment of a medical facility medical data record according to the present invention.

FIG. 1 shows an exemplary embodiment according to the present invention of a system 1 for conducting a clinical trial study. As it will be explained below in greater details, the system 1 utilizes efficient distribution and tracking techniques to minimize delays generally associated with conducting clinical trials. The system 1 may include one or more participating medical facilities 12 where patients 10 are examined. The medical facility 12 may be, for example, a hospital, a medical clinic, a physician's private office, etc. Each medical facility 12 may include one or more sources (e.g., medical equipment, medical personal) for collecting the patient's 10 medical data 204. For example, the medical facility 12 may have a radiology imaging device 9 obtaining imaging data of at least one or a portion of a patient's body. After the patient 10 is examined at the medical facility 12, the medical data 204 is collected and stored in a digital format as a Medical Facility Medical Data Record ("MFMDR") 200, as shown in FIG. 3 and further described below. The MFMDR 200 is then transmitted to a remote facility 50 via, for example, a communications network 20 (e.g., the Internet, a Wide Area Network).

The system 1 may also include a physician 8, a medical evaluator 22, a monitoring facility 14, and a clinical trial administration group ("CTAG") 16. The physician 8 may be responsible for examining the patient 10, diagnosing and prescribing treatments. The medical evaluation 22 reviews and interprets the medical data 204. In this exemplary embodiment, the radiological data would preferably be interpreted by a radiologist. The medical evaluator 22 may remote access the medical data 204 and then remotely submit the report.

The monitoring facility 14 may include a governmental agency like the U.S. Food and Drug Administration or other interested parties or sponsoring organizations. Alternatively, the monitoring facility 14 may include a clearinghouse that conducts and maintains the clinical trial study (e.g., for conducting day-to-day operations) which is initially defined by the CTAG 16. For example, the CTAG 16 may set up parameters, timelines and deadlines that the clinical trial study should operate in accordance with and which are monitored by the monitoring facility 14. Alternatively, the CTAG 16 may conduct the clinical trial study itself. However, as understood by those skilled in the art, the monitoring facility 14 may conduct the entire study and provide periodic reports to the CTAG 16.

The CTAG 16 may, for example, include a pharmaceutical company, a medical device company, and/or a research group/organization. In one embodiment mentioned above, the CTAG 16 may conduct the clinical trial study itself. In an alternative embodiment as mentioned above, the CTAG 16 may develop the clinical trial study, which will be implemented and monitored by the monitoring facility 14. The present invention allows for the CTAG 16 to more closely track the progress of the clinical trial study.

The remote facility 50 may, for example, include one or more servers 24 connected to one or more databases 26 where medical data 204 is stored. The remote facility 50 serves as a central facility where the medical data 204 from all participating patients 10 is stored and processed. The remote server 24 also provides participants of the trial study with an access to the medical data 204. The remote server 24 may, for example, notify participants of arrival of new medical data 204 and track the progress of the clinical trial study.

Figure 2:
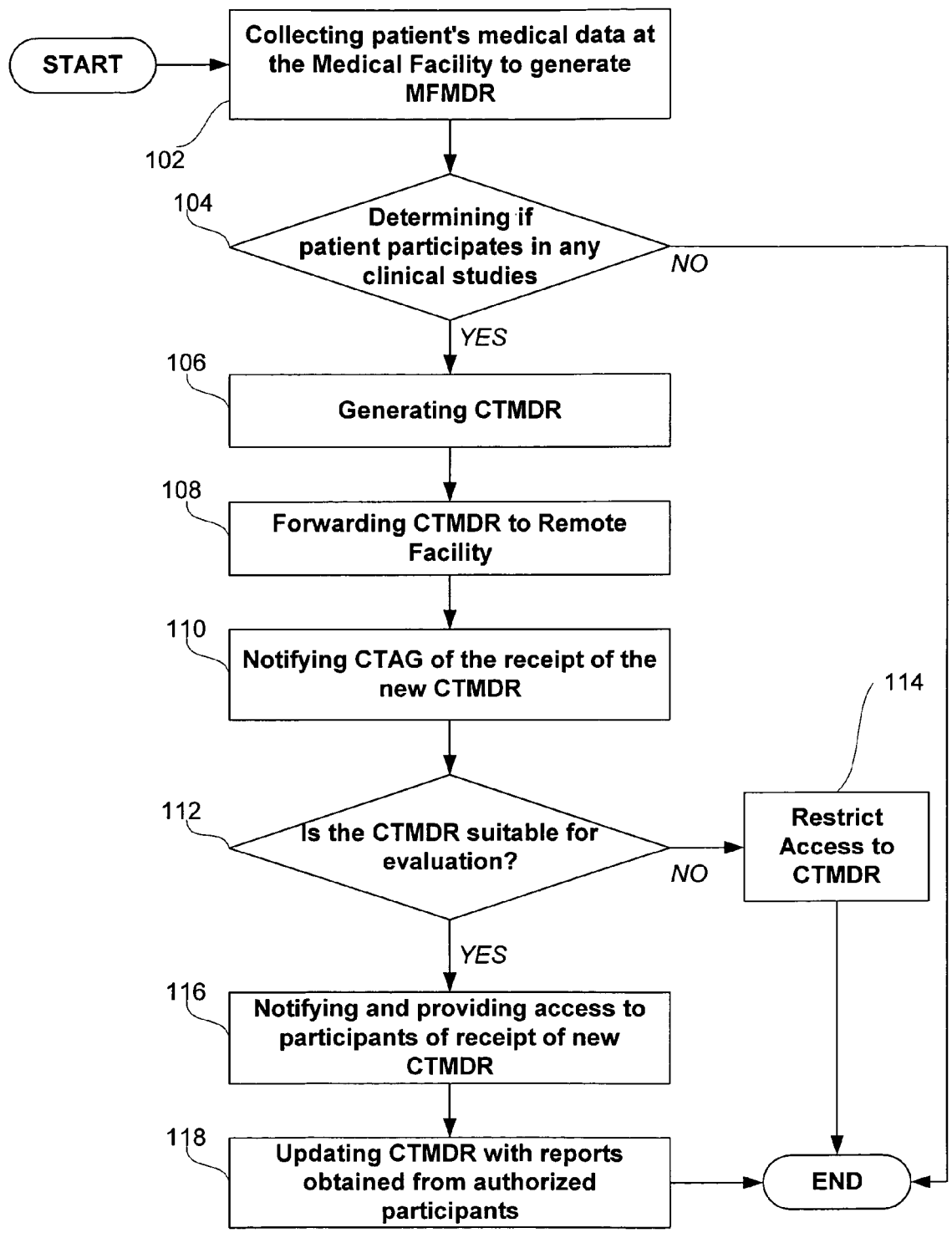
FIG. 2 shows an exemplary embodiment of a method for conducting a clinical trial according to the present invention.

FIG. 2 shows an exemplary embodiment of a method of conducting a clinical trial study. In the step 102, the medical data 204 is collected at a medical facility 12 to generate the MFMDR 200. Examinations to collect the medical data 204 may, for example, be performed by medical devices and/or medical facility personnel of the medical facility 12. Such devices may, for example, include Computerized Tomography scan, Magnetic Resonance Imaging, Positron Emission Technology, X-Rays, Vascular Interventional and Angiogram/Angiography procedures, ultrasound imaging, radiographs, optical imaging, pathological imaging, molecular imaging, medical genetic imaging and DNA imaging. Subsequent to the examination, the MFMDR 200 for the examined patient 10 is generated.

An exemplary embodiment of the MFMDR 200 is illustrated in FIG. 3, which, for example, may include, patient identification and personal information 202 (e.g., patient's name, address, social security number, date of birth, medical history, etc.), the medical data 204, a medical data type 206 (e.g., the medical data 204 includes CAT scan, etc.), examination date 208 (e.g., the medical data 204 was collected on May 1, 2004 at 2 p.m.), and a medical facility identifier 210 (e.g., the medical data 204 was collected by the medical facility 12). The medical data 204 may include a plurality of medical related such radiological data, pathology data, etc.

In step 104, the medical facility 12 determines if the patient 10 participates in any clinical trial studies. The medical facility 12 checks the patient identification information 202 against its internal database which stores a list of patients enrolled in the clinical trial studies. If the patient 10 does not participate in any clinical trials, the MFMDR 200 is stored at the medical facility 12 and no further steps need to be taken. However, if the patient 10 does participate in one or more clinical trials, the MFMDR 200 is utilized to generate a Clinical Trial Medical Data Record ("CTMDR") 212 for the patient 10 (step 106).

Figure 4A:
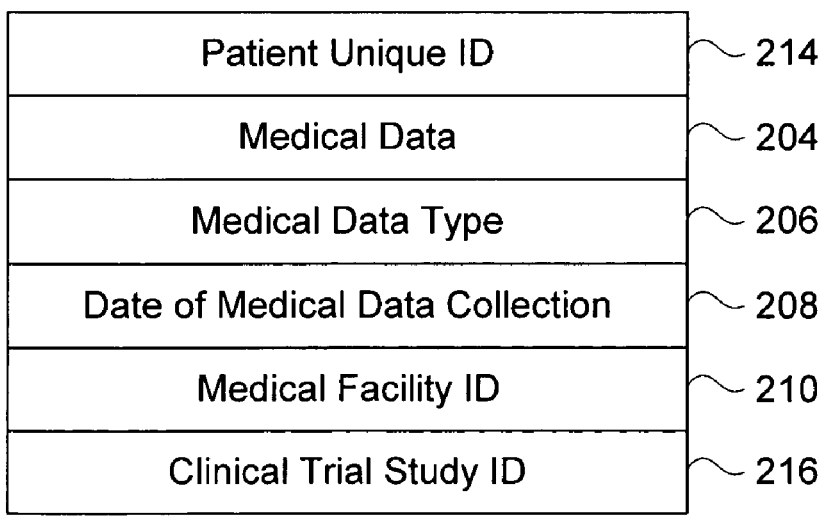
FIG. 4a shows an exemplary embodiment of a clinical trial medical data record according to the present invention.

An exemplary embodiment of the CTMDR 212 generated by the medical facility 12 is shown in FIG. 4a. The CTMDR 212 includes an unique patient identification 214, the medical data 204, the medical data type 206, the examination date 208, the medical facility identifier 210 and a clinical trial study identifier 216. During this process, the personal information 202 (e.g., name, address, social security number) of the patient 10 is at least partially removed and replaced with the unique patient identification 214. The unique patient identifier 214, for example, may be randomly generated by the CTAG 16. The unique identifier 214 provides anonymity during the transfer the CTMDR 212, preserves the patient's privacy and complies with government privacy regulations, such as, for example, the Health Insurance Portability and Accountability Act of 1996 (HIPAA).

The HIPAA imposes national standards for electronic health care transactions and national identifiers for providers, health plans, and employers. The HIPAA also mandates regulations for the security and privacy of health data. The present invention provides a system compatible with privacy requirements for handling the widespread use of electronic data interchange in health care.

In step 108, the CTMDR 212 is then forwarded to the remote server 24 via the communications network 20 where it is stored in the database 26 and accessible by authorized participants of the clinical study such the physician 8, the medical evaluators 22, etc. In step 110, the CTAG 16 is notified that the CTMDR 212 is transmitted to and received by the remote server 24. As would be understood by those skilled in the art, notification to the CTAG 16 may be provided by a transmittal notification from the medical facility 12 or a receipt notification from the remote server 24.

Upon the notification that the CTMDR 212 has been received by the remote server 24, the CTAG 16 and/or the remote server 24 may perform initial evaluation to determine if the medical data 204 of the CTMDR 212 is suitable for further review/evaluation (step 112). For example, the CTAG 16 may have in-house resources to perform the initial review on the CTMDR 212 for completeness. Alternatively, the remote server 24 may have a plurality of software modules that evaluate the medical data 204. For example, the CTMDR 212 may be unsuitable for further review/evaluation because the CTMDR 212 may be technically and/or clinically unusable. A technically unusable CTMDR 212 may include unclear information, partially damaged or corrupted files, or any other condition that would make the CTMDR 212 unreadable, unaccessible or technically unusable. A clinically unusable CTMDR 212 may indicate that the patient 10 is unsuitable for the clinical trial. For example, a specific clinical trial may require information from patients who suffer from tumors with diameters of 5 cm or larger; therefore, data from a patient with a tumor of 4.5 cm in diameter would be clinically unusable for this particular clinical trial.

In step 114, access of the authorized participants to the unsuitable CTMDR 212 may be restricted by the CTAG 16. Simultaneously, a request for transmittal or recollection of data may be sent to the medical facility 12. One of the advantages of the present invention is that it eliminates a waste of resources for the evaluation if unusable medical data and expedites collection of the replacement medical data.

Figure 4B:
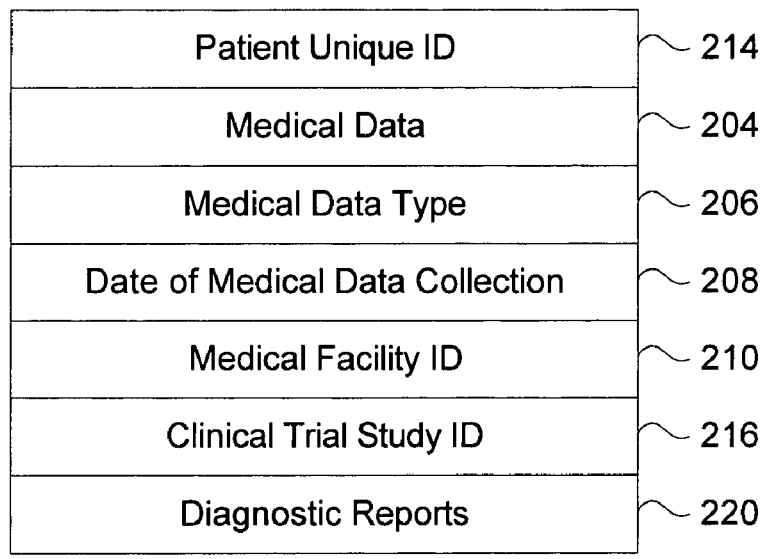
FIG. 4b shows an exemplary embodiment of an updated clinical trial medical data record according to the present invention.

Upon receipt of the suitable CTMDR 212, the remote server 24 notifies and provides access to the CTMDR 212 to the authorized participants of the clinical trial study (step 116). In step 118, each of the authorized participants accesses and reviews the CTMDR 212. Upon the review, the authorized participant generates a diagnostic report which is forwarded to the remote server 24. The remote server 24 receives the diagnostic report and generates an updated CTMDR 218 (as shown in FIG. 4b). The remote server 24 also may send a receipt notification to the CTAG 16 that the updated CTMDR 218 was received.

There may not be a specified order of the review of the CTMDR 212 by the authorized participants. For example, the physician 8 and the medical evaluator 22 may access and evaluate the CTMDR 212 at the same time. Alternatively, the physician 8 may review the medical data 204 only after the medical evaluator 22 has submitted the diagnostic report. At this point, the physician 8 may access to the updated CTMDR 218, which includes the diagnostic report 218 of the medical evaluator 22, to further evaluate the medical data 204.

Figure 5:
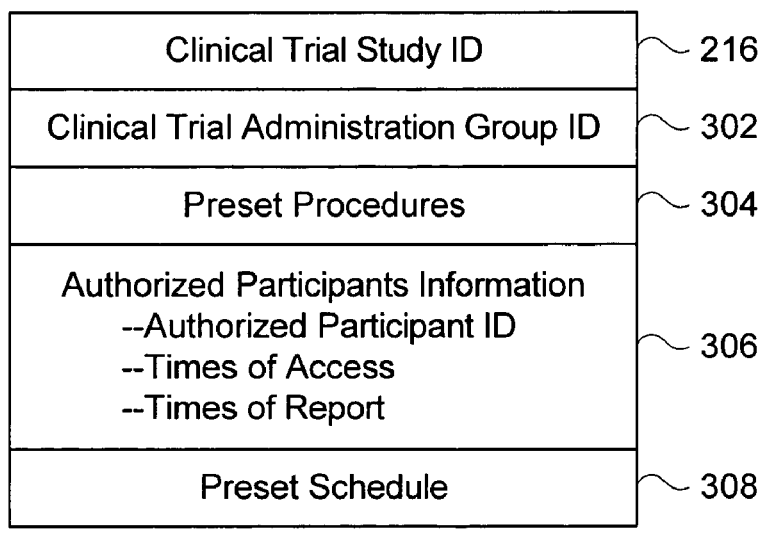
FIG. 5 shows an exemplary embodiment of a clinical trial protocol according to the present invention.

The present invention further allows the CTAG 16 to more closely track the progress of the clinical trial study. In particular, prior to the client trial study, the CTAG 16 may formulate a clinical trial protocol ("CTP") 300, as seen in FIG. 5. The CTP 300 may include the clinical trial study identifier 216, a CTAG identification 302, a preset procedure 304, an authorized participant information 306 (e.g., an identifier of the physician 8, the medical evaluator 22, etc.), and a preset clinical trial schedule 308. In other words, the CTP 300 provides a guideline for conducting the clinical study which is implemented by the remote server 24. The CTP 300 may be updated by the CTAG 16 at anytime before or during the clinical trial study.

The clinical trial study identification 216 is the same as that which appears on the CTMDR 212 and updated CTMDR 218. The clinical trial study identification 216 allows the CTAG 16 to differentiate between clinical trial studies, in the event that it is conducting multiple studies. Typically, the CTAG 16 determines the clinical trial study identification 216, which may take the form of a number, word, alphanumeric identifier or phrase. Alternatively, the CTAG 16 may provide the clinical trial study identification 216 to the remote server 24, which generates its own identification 216.

The CTAG identification 302 included in the CTP 300 allows the remote server 24 to differentiate between and correspond with multiple CTAGs 16 in the event that it is conducting multiple clinical trial studies simultaneously and for multiple CTAGs 16. The CTAG identification 302 may be generated by the remote server 24 or the CTAG 16.

The CTP 300 may further include the preset procedures 304 and the preset schedule 308 which defined the schedule and procedure of the clinical trial study. The preset procedures 304 and the preset schedule 308 are specified by the CTAG 16 based on desired goals and specifics of the study. For example, the CTAG 16 may want the medical evaluator 22 to add its diagnostic report 218 to the CTMDR 212 before the physician 8 conducts his/her evaluation; the CTAG 16 may want to review the CTMDR 212 before the physician 8 so the CTAG 16 can ask questions based on the CTMDR 212. Also, the CTAG 16 may have specified a time limit for the clinical trial study, or time limits for review by the medical evaluator 22 and/or physician 8. As would be understood by those skilled in the art, the preset procedures 304 and the preset schedule 308 are customizable based on the desires of the CTAG 16. The CTAG 16 may specify that when reminders to collect or review the medical data 204 must be sent to corresponding parties. The CTAG 16 may also set up due dates for follow up examinations of the patient 10.

Further included in the CTP 300 is the authorized participant information 306. The authorized participant information 306 may include the authorized participant's identification, a time for accessing the CTMDR 212 or updated CTMDR 218, and/or a time for reporting based on the CTMDR 212 or updated CTMDR 218. As would be understood by those skilled in the art, the authorized participant information 306 may further include as many or as few categories as the CTAG 16 deems necessary.

The authorized participant information 306 allows the remote server 24 to track the progress of the clinical trial study. For example, tracking data may be generated by monitoring the timing of access to the CTMDR 212 by authorized participants. The remote server 24 may compare the actual times of access with those in the preset schedule 308 to generate a progress report identifying delays and pointing to potential sources of the delay. For example, if the medical evaluator 22 is allotted 2 days to examine one CTMDR 212, any time taken over the allotted amount may be noted in the progress report generated by the remote server 24. Also, the remote server 24 may send a reminder notification or delay notice to the participant and the CTAG 16. The progress report may further include instances where action was taken early. For example, if the medical evaluator completes review of several CTMDRs 212 in one day, this will be noted on the progress report. This tracking feature may allow the CTAG 16 to accurately assess delays in the clinical trial study and tailor incentives and/or penalties for the authorized participants. While the tracking feature has been described as being conducted by the remote server 24, those skilled in the art would understand that the CTAG 16 and/or the monitoring facility 14 may track the clinical trial study.

Some of the CTAG guidelines/procedure may be generated during the study in the response to results obtained up to that particular point in the study. For example, results from the radiological data may generate predictions or recommendations for scheduling future patient testing based on a look up table of test results versus test schedules or other predetermined criteria.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A system for conducting a clinical trial, comprising:
   a server, in communication with the Internet or a Wide Area Network for receiving medical data, where the medical data includes image data and at least one identifier via the Internet or a Wide Area Network, the at least one identifier including an identifier linking the medical data to patient records corresponding to patients from whom the medical data was obtained; and
   a database connected to the server for storing the medical data, the database including a list of participants in the clinical trial, where the participants are also coupled to the Internet or a Wide Area Network;
   a clinical trial protocol including a plurality of preset procedures implemented in the server, where the clinical trial protocol also includes authorized participant information that allows the server to track the progress of the clinical trial study and operate to permit the participants to access the medical data via the Internet or a Wide Area Network; and
   a time tracker implemented in the remote server to track times of accessing of the medical data and times of reporting the medical data by the participants and compare actual times of access and reporting with those in a preset schedule to generate a progress report identifying delays and pointing to potential sources of the delay according to the clinical trial protocol, where transmission of the medical data and the image data is in compliance with privacy requirements for handling electronic data interchange in health care, wherein the participants include an image analyzing professional, a patient physician, a monitoring facility and a clinical trial administration group each of which are linked to the server to receive medical data through the Internet or a Wide Area Network.

2. The system according to claim 1, wherein the server generates tracking data including data indicative of times at which work product is received from the participants.

3. The system of claim 1, wherein the image data is generated by performing at least one of the following procedures: a computerized tomography scan, magnetic resonance imaging, positron emission technology, X-rays, vascular interventional and angiogram/angiography procedures, ultrasound imaging, radiographs, optical imaging, pathological imaging, molecular imaging, and medical genetic imaging.

4. The system of claim 1, wherein the image data includes at least one of photographic images, optical projection images and DNA chip images.

5. A method for conducting a clinical trial, comprising the steps of:

generating image data of at least a portion of a patient's body using a medical imaging device to perform at least one examination, where the medical imaging device is in a medical facility linked to the Internet or a Wide Area Network;

obtaining additional medical data from a patient participating in the clinical trial;

transmitting the additional medical data and the image data, through the Internet or a Wide Area Network link to a remote server, where the additional medical data includes at least one identifier, where transmission of the medical data and the image data is in compliance with privacy requirements for handling electronic data interchange in health care;

storing the additional medical data and the image data in a database accessible by the remote server in a medical data record, where the at least one identifier links the medical data record to the patient identification;

operating the remote server to implement a clinical trial protocol including a plurality of preset procedures for conducting the clinical study;

operating the remote server to give authorized participants Internet or Wide Area Network access to the medical data record according to schedules and procedures as defined by the clinical trial protocol, wherein the authorized participants include an image analyzing professional, a patient physician, a monitoring facility and a clinical trial administration group; and operating the at least one remote server to track times of accessing of the medical data and times of reporting the medical data by the participants and compare actual times of access and reporting with those in a preset schedule to generate a progress report identifying delays and pointing to potential sources of the delay according to the clinical trial protocol; and operating the at least one remote server to track progress of the clinical trial and transmission of the additional medical data and the image data according to the clinical trial protocol.

6. The method according to claim 5, wherein the at least one identifier includes no personal data of the patient.

7. The method according to claim 5, further comprising the step of providing access to the medical data record to the patient physician only after work product has been received from the image analyzing professional.

8. The method according to claim 5, further comprising the step of: generating tracking data indicative of when the medical data record was accessed and when work product was generated.

9. The method of claim 5, wherein the medical imaging device performs a radiology procedure selected from the group consisting of a computerized tomography scan, magnetic resonance imaging, positron emission technology, X-rays, vascular interventional and angiogram/angiography procedures, ultrasound imaging, radiographs, optical imaging, pathological imaging, molecular imaging, and medical genetic imaging.

10. The method of claim 5, wherein the at least one identifier includes clinical trial identification data and a facility identifier identifying a medical facility from which medical data was obtained.

11. The method of claim 5, further comprising the step of: scheduling patient testing in response to information in the medical data record.

12. The method of claim 5, wherein the medical data record includes at least one of photographic images, optical projection images and DNA chip images.

* * * * *